(12) United States Patent
Schläpfer et al.

(10) Patent No.: US 6,699,249 B2
(45) Date of Patent: Mar. 2, 2004

(54) BONE FIXATION DEVICE WITH A ROTATION JOINT

(75) Inventors: Fridolin J. Schläpfer, Glarus (CH); Martin Hess, Hölstein (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/987,388

(22) Filed: Nov. 14, 2001

(65) Prior Publication Data

US 2002/0055741 A1 May 9, 2002

Related U.S. Application Data

(63) Continuation of application No. PCT/CH99/00203, filed on May 14, 1999.

(51) Int. Cl.[7] .............................................. A61B 17/80
(52) U.S. Cl. ......................................... 606/71; 606/105
(58) Field of Search ........................... 606/69–71, 86, 606/105

(56) References Cited

U.S. PATENT DOCUMENTS

| | | | |
|---|---|---|---|
| 5,057,111 A | * 10/1991 | Park | 606/69 |
| 5,380,324 A | 1/1995 | Müller et al. | 606/61 |
| 5,470,333 A | 11/1995 | Ray | 606/61 |
| 5,616,142 A | * 4/1997 | Yuan et al. | 606/61 |
| 5,707,372 A | 1/1998 | Errico et al. | 606/61 |
| 5,964,762 A | 10/1999 | Biedermann et al. | 606/69 |
| 6,325,803 B1 | * 12/2001 | Schumacher et al. | 606/71 |
| 6,336,927 B2 | * 1/2002 | Rogozinski | 606/61 |
| 6,340,362 B1 | * 1/2002 | Pierer et al. | 606/71 |
| 6,379,354 B1 | * 4/2002 | Rogozinski | 606/61 |

FOREIGN PATENT DOCUMENTS

| | | |
|---|---|---|
| DE | 44 38 264 | 3/1996 |
| EP | 0 829 240 A1 | 3/1998 |
| FR | 2 726 459 | 5/1996 |
| WO | WO 94/06360 | 3/1994 |

\* cited by examiner

*Primary Examiner*—Kevin Shaver
*Assistant Examiner*—Michael B. Priddy
(74) *Attorney, Agent, or Firm*—Pennie & Edmonds LLP

(57) ABSTRACT

The invention relates to a bone fixation device which includes a pair of bone plates and a longitudinal carrier. The longitudinal carrier can be used to permit the bone plates to telescope with respect to one another, such as in a direction parallel to the longitudinal axis of the vertebral column. A joint also may be used to permit swivelling of the plates with respect to each other.

47 Claims, 5 Drawing Sheets

BONE FIXATION DEVICE WITH A ROTATION JOINT

CROSS-REFERENCE TO RELATED APPLICATIONS

This application is a continuation of the U.S. national stage designation of copending International Patent Application PCT/CH99/00203, filed May 14, 1999, the entire content of which is expressly incorporated herein by reference thereto.

FIELD OF THE INVENTION

The present invention relates generally to orthopaedic fixation devices, and in particular to a fixation system for vertebral bodies.

BACKGROUND OF THE INVENTION

Operations of spinal conditions occurring in the area of the lumbar or thoracic vertebral column may be carried out using an anterior approach. Such an approach may be beneficial because pathological processes often affect the anterior column of the spine. Access to the spinal cord also may be easier to achieve via anterior rather than posterior surgical approaches. Additionally, decompressing the spinal cord may be accomplished more simply or effectively by using an anterior approach. The mechanics of supporting the anterior column may also provide a superior alternative to posterial lateral fixation or fusion. Further, as fewer muscular, neurological and vascular structures may be damaged during spinal surgery using an anterior technique—as compared to a posterior approach—patients can benefit from fewer complications and enjoy faster recovery due to less trauma surrounding the surgical site. Accordingly, new and innovative techniques for treating the spine via anterior approach techniques are being developed.

One internal anterior fixation system for the treatment of vertebral burst fractures known from the related art is disclosed in WO 94/06360 to Danek. This fixation system includes an elongated plate having integral superior, inferior and bridge portions. The superior and inferior portions are provided for fixation to corresponding vertebrae with the bridge portion spanning between the portions over the affected vertebra. The superior portion includes a pair of generally parallel elongated slots, each having scallops for receiving bone fixation screws or bolts. The inferior portion includes a pair of openings through which fixation screws or bolts extend. The slots in the superior portion allow for compression or distraction of the intermediate vertebral region. The openings in the inferior portion are oriented at an oblique angle relative to the longitudinal axis of the plate to provide a quadrilateral fixation construct. The bridge portion has a width significantly less than the width of the superior and inferior fixation portions. In certain embodiments of this known fixation system, the two posterior bone screws may be inserted prior to the implantation of the bone plate. After the insertion of the two bone screws, the bone plate is introduced into the patient's body through a small incision, placed onto the bone screws, and fastened thereon by means of nuts. Once the bone plate has been fixated, the two anterior screws are screwed into the bone plate through corresponding screw holes.

Another fixation system for vertebral bodies which permits contraction or distraction of parts to be connected during an operation is known from EP 0 829 240 to Harms. This known bone plate comprises a first portion having an elongated hole, extending in the longitudinal direction of the intermediate portion and a second portion having bores, and being connectable with the first portion. A screw connecting the two portions is provided and guided through the elongated hole, for connecting the two portions. One of the portions comprises a structured surface, and the other portion comprises a recess for registering therewith. A fixating element is provided for engagement with the structure for locking the relative position of the two portions relative to each other. Due to the elongate holes, the overall length of the plate is variably adjustable.

Additionally, U.S. Pat. No. 5,707,372 discloses a variable length cross-link device which may be affixed to the rods of a dual rod implant apparatus, or to the heads of opposing pedicle screws through which such rods are positioned. The device is capable of assuming variable length and a variable angulation.

Also, U.S. Pat. No. 5,470,333 discloses a system for stabilizing the cervical and the lumbar region of the spine with an anatomically correct curvature.

Despite these developments, a need exists for an anterior fixation system for vertebral bodies that allows manipulation of the vertebrae for correcting malpositions, which includes the possibility of length adjustment over a long distance, and which permits lordosis and kyphosis formation in vivo even after the implant has been placed.

SUMMARY OF THE INVENTION

The invention is related to a fixation device for connecting bone portions. The fixation device includes a first plate and a second plate, each plate having a top surface, a bottom surface for contacting bone, and a fixation bore extending from the top surface to the bottom surface. At least one member is telescopically associated with at least one of the plates. The fixation device also includes a releasably lockable joint. The at least one member permits translation of the plates with respect to each other about a translation axis, and the releasably lockable joint permits swivelling of the plates with respect to each other about a swivel axis oriented transverse to the translation axis.

In some embodiments, the releasably lockable joint includes a first clamping member disposed in a sleeve, with the first clamping member being configured and dimensioned to exert a force against the sleeve. The releasably lockable joint may further include a straining member such as a fastener for translating the first clamping member with respect to the sleeve. At least a portion of the sleeve may be resiliently deformable, and each fixation bore may be disposed at an angle of about 60° to about 90° with respect to the bottom surface. Also, at least a portion of the sleeve and at least a portion of one of the plates may be configured and dimensioned for positive engagement with respect to each other. The sleeve may be disposed in a bore, with the sleeve and bore each having a plurality of teeth for providing positive engagement.

At least one member may be releasably lockable with at least one of the plates. The releasably lockable joint may further include a second clamping member disposed in the sleeve, with the second clamping member being configured and dimensioned to exert a force against the sleeve. The straining member may be associated with the second clamping member to permit translation of the second clamping member with respect to the sleeve, and the straining member may be threadably associated with the first and second clamping members to permit the members to axially translate with respect to each other.

At least one of the clamping members may have a wedge-shape. The first clamping member may include a wedge shape and the sleeve may include a slot configured and dimensioned to positively receive the first clamping member. The first clamping member may mate with a slot disposed in the sleeve. Also, the first clamping member may include a hole and the fastener may be threadably associated with the hole. The fastener may be axially fixed with respect to the sleeve. In some embodiments, the sleeve and the first clamping member have complementary conical portions.

In order to permit rotation of at least one component selected from the first plate, the second plate, and the at least one member about the swivel axis, a recess may be provided for positive engagement with a tool.

The fixation device may further include at least two fixation members, wherein at least one fixation bore in each plate receives a fixation member for coupling the plate to bone. At least one of the fixation members may be selectably angulated with respect to the bottom surface of a plate.

At least one fixation bore may include a spherical portion, and the fixation device may further include at least one fixation member having a head with a spherical portion. The spherical portion of the head may be sized to rest in the spherical portion of the fixation bore to permit angulation of the fixation member in the fixation bore. The spherical portions may be mutually roughened, structured, or toothed, and the head may be slotted and resiliently deformable. The fixation device may further include a straining member for circumferentially deforming the head, and the head may have a threaded inner cone threadably associated with the straining member.

A collet chuck may be provided, including an outer spherical portion, so that the spherical portions of the at least one fixation bore and collet chuck mate to permit angulation of the portions with respect to each other. The collet chuck may further include a through hole for receiving a fixation member. The through hole may have a first taper, the fixation member may have a second taper, and the tapers may be complementary.

The swivel axis may be oriented substantially perpendicular to the bottom surface of at least one of the plates. Further, the releasably lockable joint may include a shaft coupled to one of the plates and one of the at least one member, with the shaft permitting rotation of the plate with respect to the member. At least a portion of the shaft may be configured and dimensioned for positive engagement with at least one of the plate and the member.

The invention also relates to a fixation device for connecting bone portions including: a first plate and a second plate, each plate having a top surface, a bottom surface for contacting bone, and a fixation bore extending from the top surface to the bottom surface; at least one member telescopically and slidably associated with a channel in at least one of the plates; and a releasably lockable joint. The at least one member permits translation of the plates with respect to each other about a translation axis, and the releasably lockable joint permits swivelling of the plates with respect to each other about a swivel axis oriented transverse to the translation axis.

The invention further relates to a fixation device for connecting bone portions including: first and second plates, each plate having a top surface, a bottom surface for contacting bone, and a fixation bore extending from the top surface to the bottom surface; first and second members, each member being telescopically and slidably associated with the first plate; and a joint defining a first axis and including a clamping member disposed in a sleeve. The members permit translation of the plates with respect to each other, the joint permits angulation of one of the plates with respect to at least one of the members about the first axis, and the clamping member is actuable with respect to the sleeve to releasably fix the angulation.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
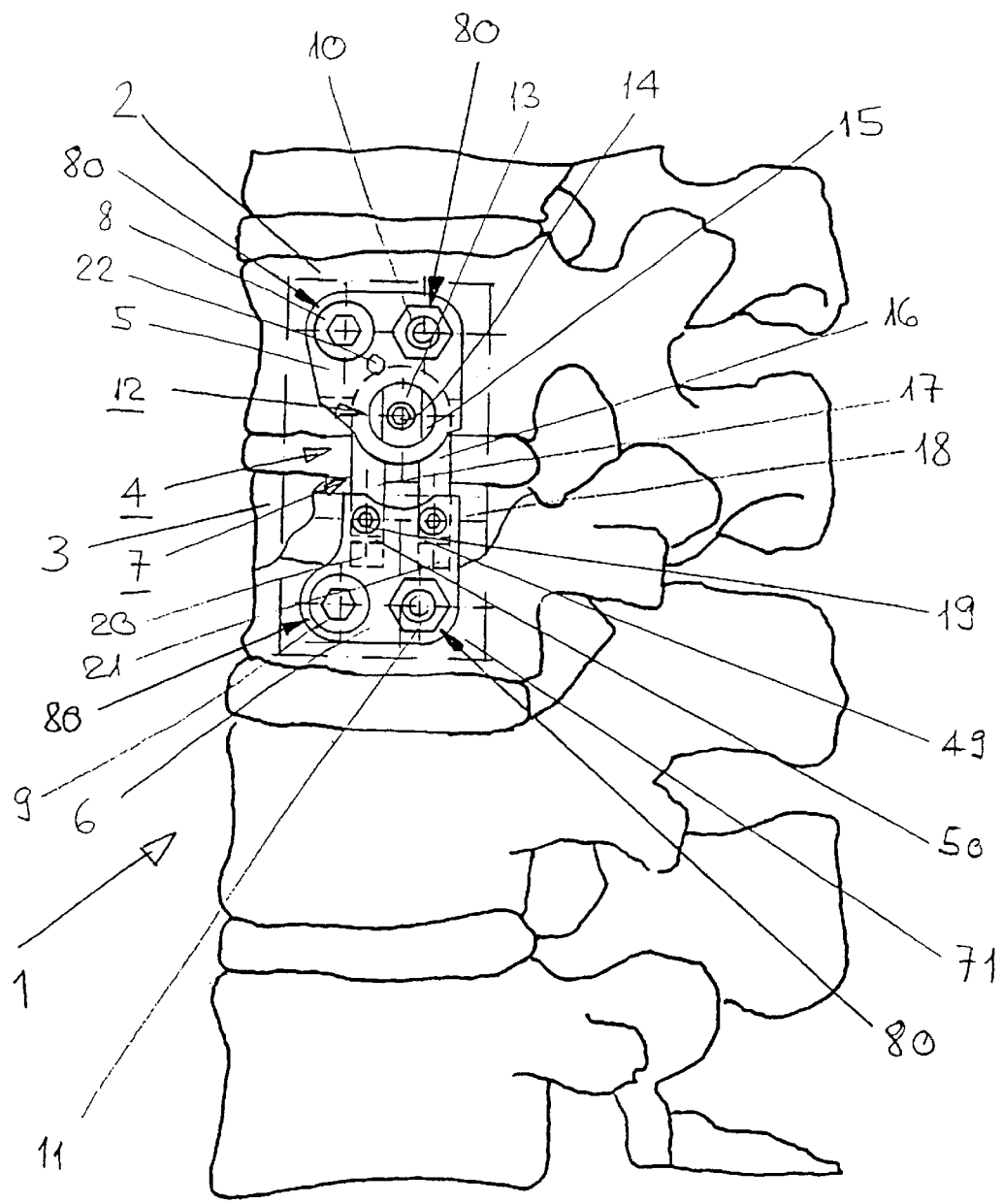
FIG. 1 is a lateral view of part of a vertebral column provided with an exemplary embodiment of the fixation device according to the invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto.

Advantages offered by the present invention generally include: allowing manipulation of the vertebrae for correcting malpositions; providing a fixation system capable of length adjustment over a long distance; and the capability of lordosis and kyphosis formation in vivo after the implant has been placed.

FIG. 1 shows an exemplary embodiment of the bone fixation device 4 according to the invention which has been applied mono-segmentally to a vertebral column 1. The bone fixation device 4 may be used to connect a cranial vertebra 2 to a partially injured caudal vertebra 3. The bone fixation device 4 generally includes a cranial bone plate 5, a caudal bone plate 6, and a longitudinal carrier 7. The cranial and the caudal bone plates 5,6 each can have a bottom surface 29 which contacts bone and a top surface 52. The two bottom surfaces of the bone plates 5,6 may lie within a common surface 71. The longitudinal carrier 7 can be used to connect the cranial bone plate 5 and the caudal bone plate 6 in such a way as to allow the bone plates 5,6 to telescope with respect to one another. For example, the longitudinal carrier might be used to allow the plates 5,6 to telescope in a direction parallel to the longitudinal axis of the vertebral column. The longitudinal carrier may also be used to allow the plates 5,6 to be capable of swivelling about a joint 12. For instance, the axis of rotation 27 about a joint 12 may extend substantially perpendicular to the common surface 71, defined by the bottom surfaces 29 of the bone plates.

Generally, the bone plates 5,6 may be fastened to the vertebrae 2,3 by suitable fixation elements. For instance, one anterior bone screw 8,9 and one posterior bone screw 10,11, respectively, may be used. Other examples of potentially suitable fixation elements include, without limitation, bolts and blind rivets.

As described above, the swivelling capacity of the cranial bone plate 5 relative to the longitudinal carrier 7 may be achieved by means of a joint 12. Preferably, the joint 12 may be lockable. For instance, the joint 12 may be capable of preventing relative rotation between the cranial bone plate and the longitudinal carrier 7 by means of a clamping wedge 13 and a straining screw 14, which may also be used to connect the longitudinal carrier 7 to the cranial bone plate 5. For example, the straining screw 14 may be used to cause the clamping wedge 13 to be displaced relative to a sleeve 15 mounted within the cranial bone plate 5. In response, the sleeve 15 may deform radially or in some other predetermined fashion. The deformation of the sleeve, preferably, may be resilient.

The sleeve 15 and the longitudinal carrier 7 may be connected by means of a non-positive or positive engagement. For example, in one embodiment of the locking mechanism of the joint 12, the clamping wedge 13 may press the resiliently deformable segment of the sleeve 15 against the wall of the bore arranged in the cranial bone plate 5 and establish a non-positive engagement means by which the joint 12 is locked. Conversely, the straining screw 14 may be used to cause the clamping wedge 13 to deform a suitably designed sleeve 15 into one or more recesses within the wall of the bore to establish a positive engagement means by which the joint 12 is locked.

The capability of the bone fixation device 4 to distract or telescope may be advanced by the design of the longitudinal carrier 7. For instance, in one embodiment the longitudinal carrier 7 may take the form of two parallel rods 16,17 which are capable of relative motion with respect to corresponding guide channels 20,21 arranged in the caudal bone plate 6. The relative motion between the longitudinal carrier 16,17 may be, without limitation, continuous and sliding relative motion, incrementally driven relative motion, or a combination thereof. In the exemplary embodiment shown in FIG. 1, the two parallel rods 16,17 can be fastened within their corresponding guide channel 20,21 by means of two set screws 18,19.

Additionally, the cranial bone plate 5 may be equipped with a hexagon socket 22 into which a screw driver or similar tool may be inserted so as to exert a torsional moment on the cranial bone plate 5. If, however, the rotation joint 12 is in a locked configuration the torsional moment may be exerted on the bone fixation device 4.

Also, the rods 16,17 may be provided with projections 49,50 formed in their end portions after the rods have been inserted into the caudal bone plate 6 in order to prevent the longitudinal carrier 7 from slipping out while the set screws 18,19 are released.

Figure 2:
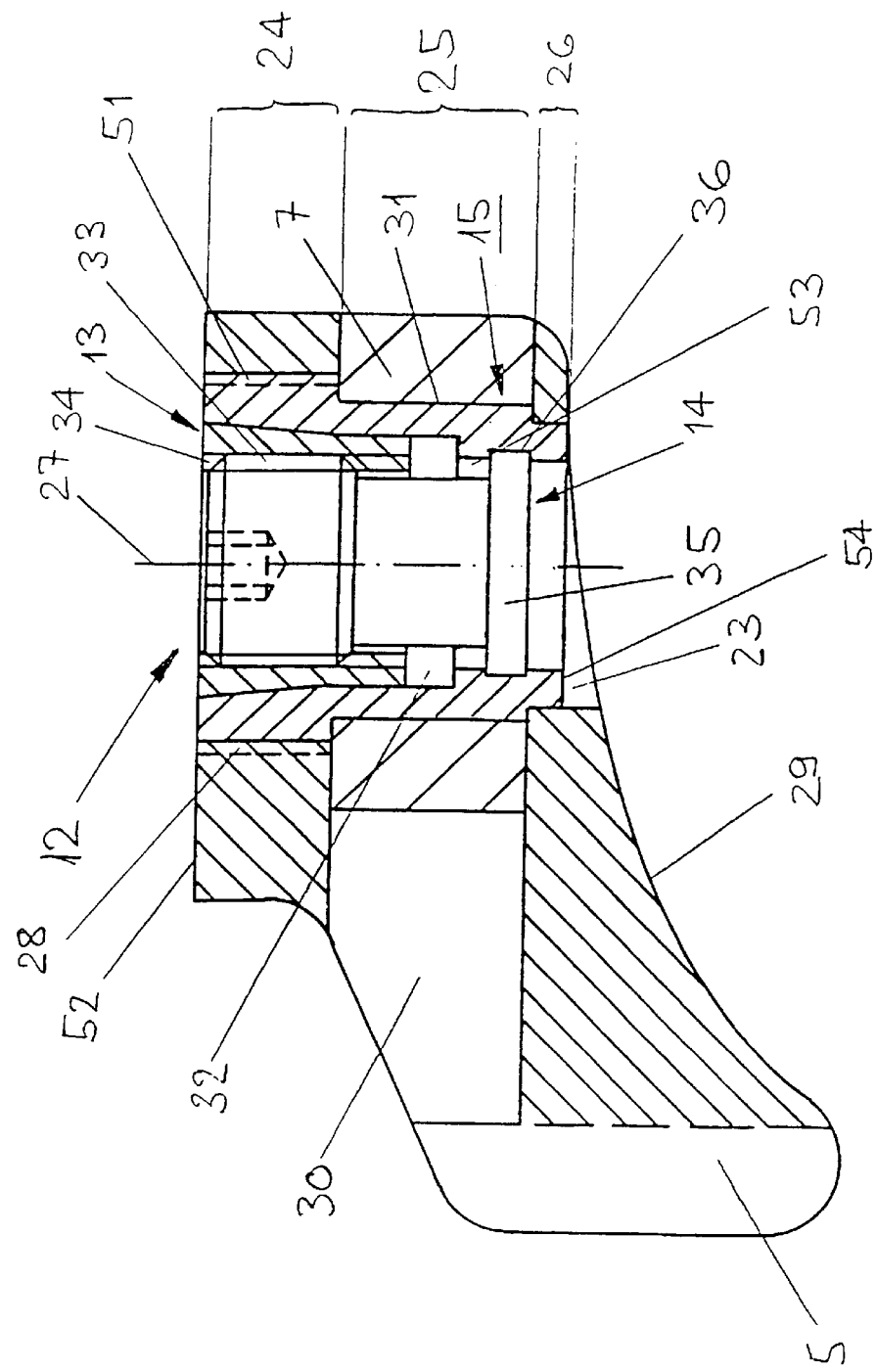
FIG. 2 is a cross-sectional view taken perpendicular to the longitudinal axis of the vertebral column and showing one embodiment of the fixation device of FIG. 1, as seen in the area of the rotation joint.

FIG. 2 is a cross-sectional view taken perpendicular to the longitudinal axis of the vertebral column showing the cranial bone plate 5 and the joint 12 of one embodiment of the device of FIG. 1. The joint 12 comprises a cylindrical sleeve 15, a clamping wedge 13, and a straining screw 14.

In general, the cranial bone plate 5 is shaped concavely on its bottom surface 29 for adjoining the cranial vertebral body 2. A bore 23 in the cranial bone plate 5 may further extend from the top surface through the bottom surface 29 of the cranial bone plate 5. The bore can further have a central axis 27 which is substantially perpendicular to the bottom surface 29 of the cranial bone plate 5. A groove 30 within the cranial bone plate 5 that extends perpendicular to the central axis 27 may open toward the caudal bone plate 6 and receive the longitudinal carrier 7. For example, the longitudinal carrier 7 may be provided with a bore 31 extending concentrically to the central axis 27 and which is adequately dimensioned so that a non-positive engagement by means of a press fit is realized between the central portion 25 of the sleeve 15 and the bore 31. Alternatively, a positive engagement means such as a tongue and groove connection or a toothing may be used for this purpose.

The portion of the cranial bone plate 5 extending between the groove 30 and the bottom surface 29, the bore 23 may further be shaped in such a way that the segment 26 of the sleeve 15 adjoining the bone may be rotatably mounted therein. Additionally, the segment 24 of the sleeve 15 distant from the bone may be fitted into the part of the bore 23 formed in the cranial bone plate 5 that faces equally away from the bone. The part of the bore 23 distant from the bone may be further provided with a toothing 28 the profile of which corresponds to that of the toothing 51 arranged in the segment 24 of the sleeve 15 distant from the bone. In a first configuration, a positive engagement may be realized between the sleeve 15 and the bore 23 as the clamping wedge 13 is forced sufficiently far into a partially wedge-shaped slot 32. Specifically, the slot 32 may extend perpendicular to the central axis 27 so that the segment 24 of the sleeve 15 distant from the bone is spread apart to such an extent that the toothings 28,51 will engage with each other as the clamping wedge 13 is advanced to produce a rotationally positive engagement between the sleeve 15 and the longitudinal carrier 7. By contrast, in a second configuration when the clamping wedge 13 is sufficiently withdrawn from the slot 32, the toothings 28,51 do not engage with each other, so that the sleeve 15 together with the longitudinal carrier 7 is freely rotatable in the bore 23 about the central axis 27.

In FIG. 2 the displacement of the clamping wedge 13 parallel to the central axis 27 may be affected by means of the straining screw 14. For instance, the straining screw 14 may be provided with an external screw thread 33 distant from the bone, while also having a projection 35 on its part adjoining the bone. The straining screw can then be advanced within the clamping wedge 13, which may further be provided with a mating internal thread 34. In this manner, the straining screw can controllably affect the displacement of the clamping wedge 13 and provide a means for changing the configuration of the joint from a locked and unlocked position. Additionally, the sleeve 15 may have an annular groove 36, which may be formed by rolling in the end portion 54 of the sleeve 15, after the straining screw 14 is introduced into the bore 53 of the sleeve 15.

Figure 3:
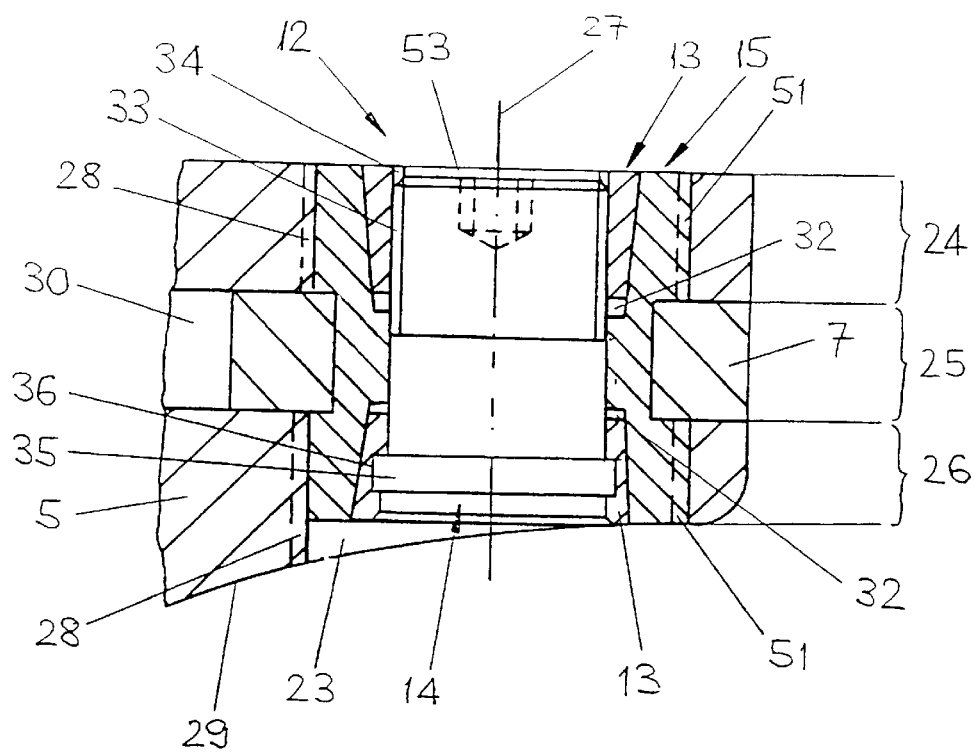
FIG. 3 is a cross-sectional view taken perpendicular to the longitudinal axis of the vertebral column showing another embodiment of the fixation device of FIG. 1, as seen in the area of the rotation joint.

FIG. 3 shows an illustrative embodiment of the joint 12 with two locking mechanisms. In this embodiment, the first locking mechanism may comprise the positive engagement means described in the embodiment of FIG. 2 and further include a second locking mechanism which may be located within a segment 26 of the sleeve 15 adjoining the bone. The second locking mechanism may also include a partially wedge-shaped slot 32 extending perpendicular to the central axis 27 and a clamping wedge 13 that may be provided to cooperate with the second partially wedge-shaped slot 32 to affect the configuration of the joint between a locked position and an unlocked position.

Likewise, the segment 26 of the sleeve 15 adjoining the bone, may be provided with a positive engagement means such as an external toothing 51, and the bore 23 may be provided with a recess 28 corresponding to this toothing 51 so that a positive engagement is realized between the sleeve 15 and the bore 23 in the segment 26 of the sleeve 15 adjoining the bone as the second wedge 13 is pressed sufficiently far into the slot 32. In this manner, the segment 26 of the sleeve 15 adjoining the bone may be spread apart to such an extent that the toothing 28 engages with recess 51 to prevent relative motion about the joint 12. Thus in one configuration, the clamping wedges 13 form themselves a rotationally positive engagement between the sleeve 15 and the longitudinal carrier 7, which prevents rotation about the joint 12. In a second configuration, however, where the clamping wedges 13 are in a released condition the respective toothings 28 and recesses 51 do not engage with each other, so that the sleeve 15 is freely rotatable within the bore 23 about the central axis 27.

As previously described, the displacement of the clamping wedges 13 parallel to the central axis 27 may be realized by means of the straining screw 14 which on its part distant from the bone is provided with an external screw thread 33 and on its part adjoining the bone with a projection 35. This arrangement of the clamping wedges 13, the straining screw 14, and the sleeve 15 allows the two clamping wedges 13 to be moved towards each other as the straining screw 14 is tightened, so that the two resiliently spreadable segments 24,26 of the sleeve 15 are pressed against the wall of the bore 23 thus bringing the external toothing 28 formed in the sleeve 15 into engagement with the complementary recess 51 formed in the bore 23. As the straining screw 14 is released, the clamping wedges 13 are moved away from each other, causing the two resiliently deformable segments 24,26 of the sleeve 15 to move back towards their initial positions until the respective toothings 28 and recesses 51 are no longer in engagement with each other, so that the sleeve 15 is freely rotatable within the bore 23 about the central axis 27. As noted above, the annular groove 36 may be formed after introduction of the straining screw 14 into the bore 53 of the sleeve 15 by rolling in the wall of the clamping wedge 13 adjoining the bone.

In another embodiment of the device according to the invention (not shown) the freely rotatable yet axially fixed connection between the straining screw 14 and the sleeve 15 may be replaced by a freely rotatable yet axially fixed connection between the straining screw 14 and the clamping wedge 13 adjoining the bone. For instance, the projection 35 formed in the straining screw 14 and an annular groove formed in the clamping wedge 13 adjoining the bone may be provided in substitution of the threaded connection between the external right-hand thread 56 of the straining screw 14 and the internal right-hand thread 55 of the clamping wedge 13 adjoining the bone.

Figure 4:
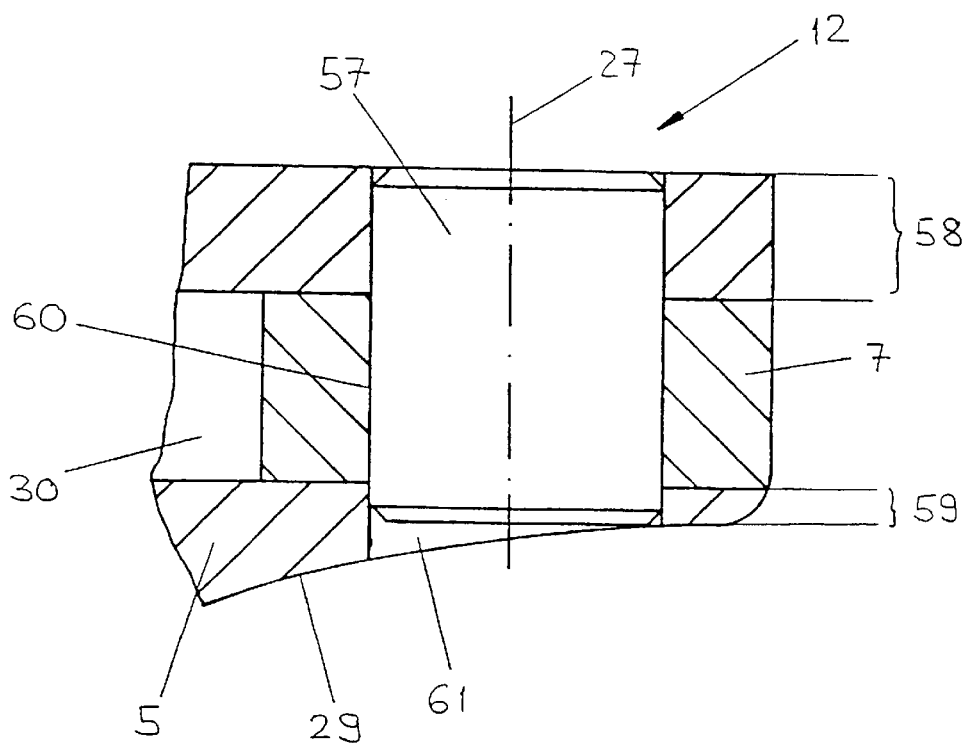
FIG. 4 is a cross-sectional view taken perpendicular to the longitudinal axis of the vertebral column showing one embodiment of the fixation device of FIG. 1, as seen in the area of the bone screws.

FIG. 4 shows yet another embodiment of the joint 12 of the device according to the invention. In this general embodiment of joint 12, a shaft 57 may be mounted in a bore 61 which may extend essentially vertically from the top surface to the bottom surface 29 of the plate 5. In general, the shaft 57 may be mounted in a bore 61 in the segment 59 of the plate 5 adjoining the bone or in a segment 58 thereof distant from the bone. Alternatively, a longitudinal carrier 7 comprising the shaft 57 may be equally mounted in a bore 60. Concerning the rotatability and/or the force fit of the shaft 57 in the bores 60,61, the following illustrative non-limiting variants are possible. In one example, the shaft 57 may be anchored by means of positive or non-positive engagement in the bore 60 arranged concentrically to the axis of rotation 27 in the longitudinal carrier 7 while being rotatably mounted in the bore 61 arranged concentrically to the axis of rotation 27 in the plates PA and PB 5,6, respectively.

In another example, the shaft 57 may be anchored by means of positive or non-positive engagement in the bore 61 arranged concentrically to the axis of rotation 27 in the plates PA and PB 5,6, respectively, while being rotatably mounted in the bore 60 arranged concentrically to the axis of rotation 27 in the longitudinal carrier 7.

Figure 5:
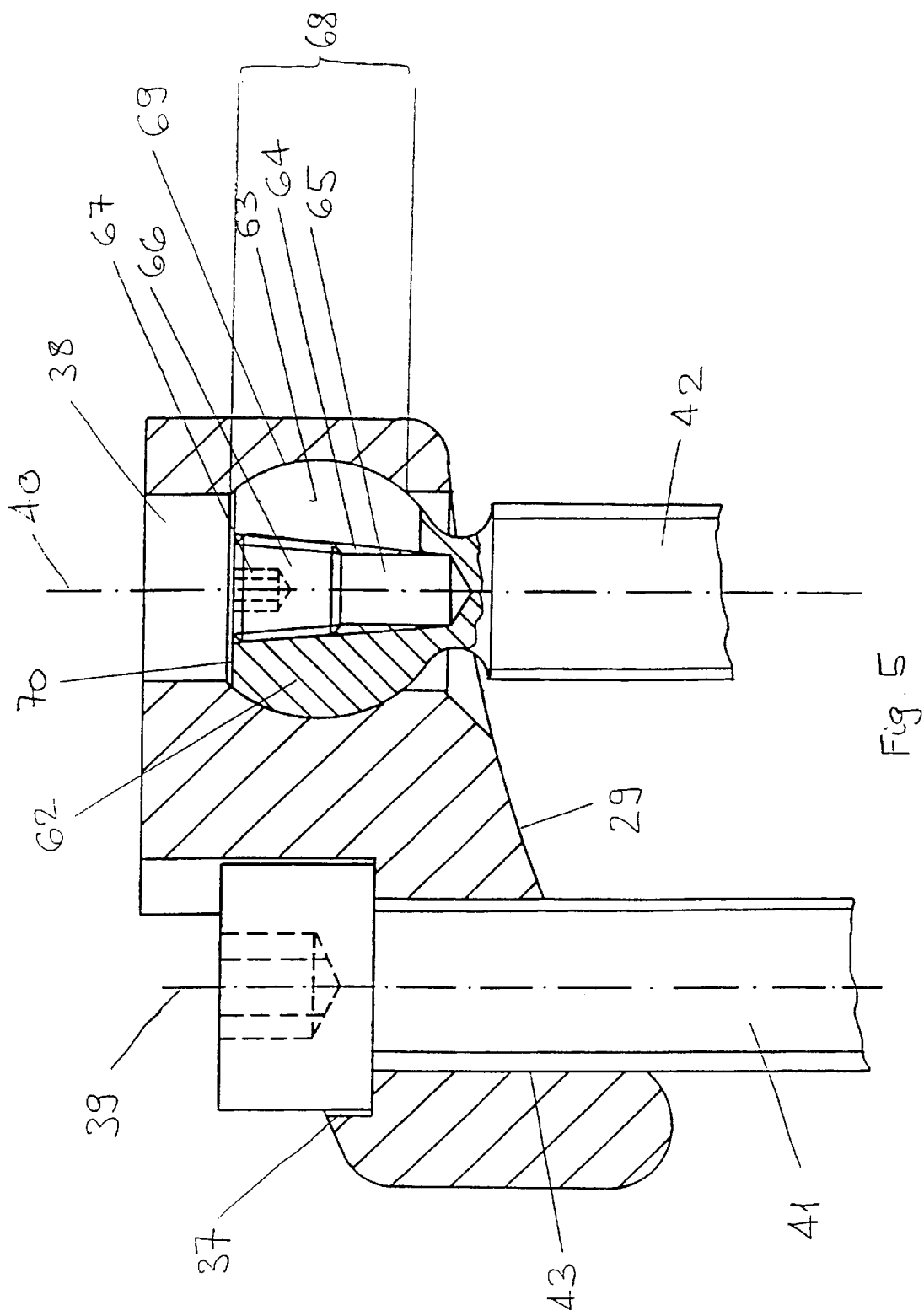
FIG. 5 is a cross-sectional view taken perpendicular to the longitudinal axis of the vertebral column showing another embodiment of the fixation device of FIG. 1, as seen in the area of the bone screws.

FIG. 5 is a cross-sectional view taken perpendicular to the longitudinal axis of the vertebral column showing an embodiment of the cranial bone plate 5 through the bores 37,38. In use, the bores may be used for receiving suitable fastening elements such as bone screws 41,42. For instance, the longitudinal axes 39,40 of the bores 37,38 may extend essentially vertically to the bottom surface 29 of the cranial bone plate 5 adjoining the vertebral body so that the anterior bone screw 41 may be screwed into a bore 37 within the cranial bone plate 5 and then advanced into the cranial vertebral body 2. The bore 37 may also be provided with an internal screw thread 43. The posterior bone screw 42 may similarly be advanced through a second bore 38 and then advanced into the cranial vertebral body 2.

Alternatively, the posterior bone screw 42 may be fixated within the plate 5 by means of a spherical screw head 62 which is resiliently pressable against the wall 69 of a spherical recess 68 formed in the bore 38 and of a conical straining screw 66 which permits screw head 62 to be spread apart. The elasticity of the spherical screw head 62 may be obtained by means of a plurality of radial slots 63 extending perpendicular to the longitudinal axis 40 of the bone screw 42 and leading to the end portion 70 of the bone screw 42 distant from the bone. From that same end portion 70 of the bone screw 42 distant from the bone, a bore 65 with a conical, internal screw thread 64 extending concentrically to the longitudinal axis 40 may penetrate into the screw head 62. For spreading apart the screw head 62 so as to lock it tightly within the spherical recess 68 formed in the bore 38 of the plate 5, the conical straining screw 66 may be provided with a means for receiving a tool such as a screw driver for advancing the straining screw 66 into the bore. For instance, the head of straining screw 66 may be provided with as a hexagon socket 67 that can be screwed into the conical, internal thread 64 of the screw head 62. Due to this screw head design the posterior bone screw 42 may be locked within the plate even at an oblique angle relative to the longitudinal axis 40.

In another embodiment of the device according to the invention (not shown), the spreading apart and locking of the resilient screw head 62 may be realized in such a way that the accommodation for receiving the straining screw consists of an inner cone divergent toward the opening of the bore, an internal screw thread located further down the opening of the bore and adjacent thereto, and a straining member which can be a screw having a male taper and an external thread complementary to the inner cone and the external thread thereon.

Figure 6:
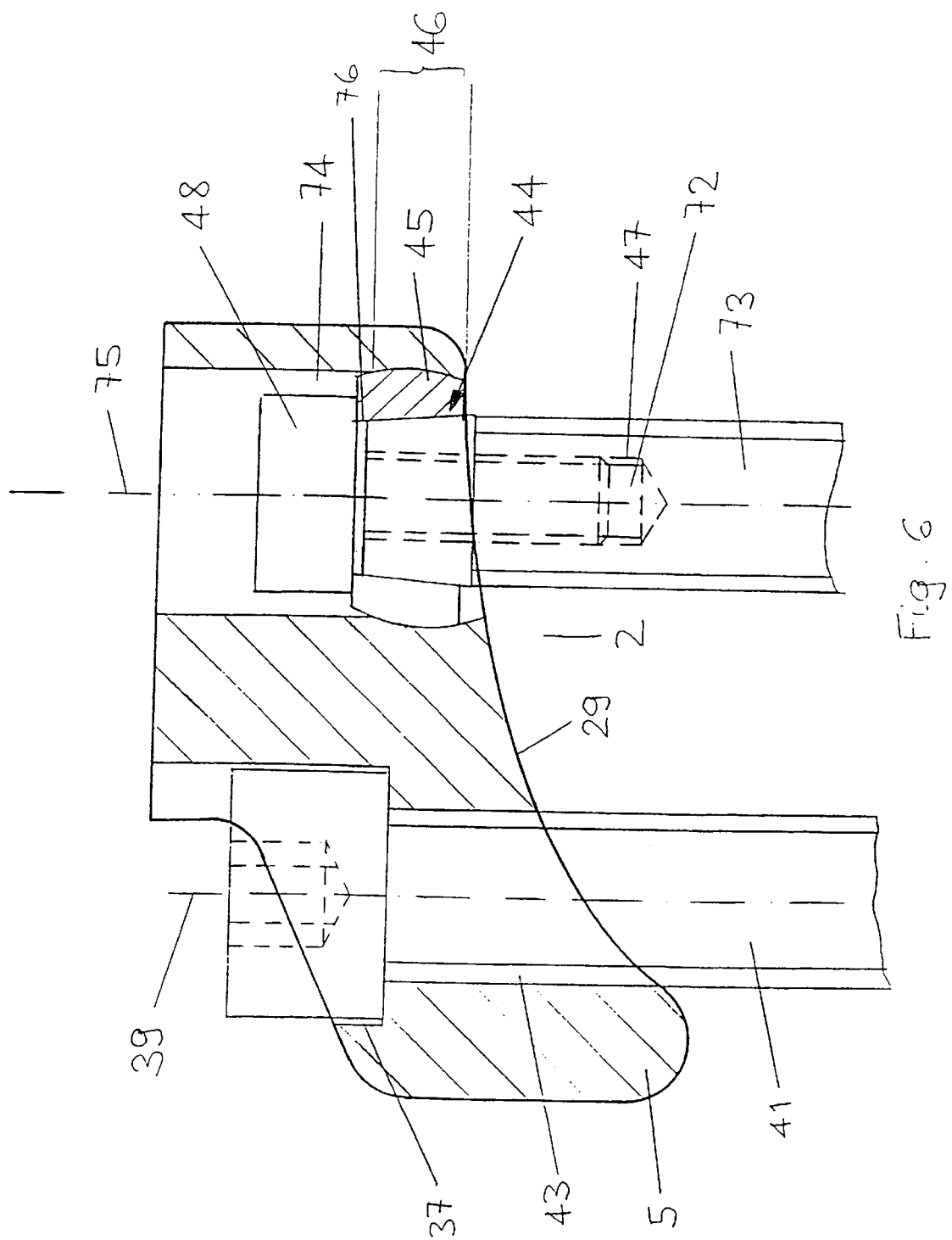
FIG. 6 is a cross-sectional view taken perpendicular to the longitudinal axis of the vertebral column showing another embodiment of the fixation device of FIG. 1, as seen in the area of the bone screws.

FIG. 6 is a section perpendicular to the longitudinal axis of the vertebral column showing another embodiment of the cranial bone plate 5 through the bores 37,74. In use, the bores may be used for receiving suitable fastening elements such as bone screws 41,73. For instance, the longitudinal axes 39,75 of the bores 37,74 may extend essentially vertically to the bottom surface 29 of the cranial bone plate 5, adjoining the surface of the vertebral body 2 so that the anterior bone screw 41 may be screwed into a bore 37 within the cranial bone plate 5 and then advanced into the cranial vertebral body 2. The bore 37 may also be provided with an internal screw thread 43. The posterior bone screw 73 may similarly be advanced through a second bore 74 and then advanced into the cranial vertebral body 2.

The posterior bone screw 73 may be fastened within the bone plate by means of a conical connection 44 within a collet chuck 45 that can be shaped in the form of a spherical segment. The collet chuck 45 may be mounted in such a way in a spherical segment 46 of the bore 74 that it is axially fixed while being capable of swivelling about the center of the sphere. The posterior bone screw 73 can be firmly kept in place by means of a screw 48 which may be screwed into the internal screw thread 47 that is arranged in the bore 72 formed in the end portion of the bone screw 73 distant from the bone. The fixation of the posterior bone screw 73 may be realized by tightening the screw 48, which causes the collet chuck 45 to be expanded through the wedge-like action of the conical connection 44 and to be pressed against the wall of the spherical segment 46 of the bore 74. Due to this design, the posterior bone screw 73 may be locked within the plate even at an oblique angle relative to the longitudinal axis 75.

Referring back to FIG. 1, the bores 37,38,74 within the caudal bone plate 6 may be arranged in a laterally reversed disposition with respect to the bores in the cranial bone plate. Additionally, in the embodiments of the device according to the invention shown in FIGS. 2 and 3, the clamping wedges 13 may be replaced by clamping cones. In this case, the recess 32 formed in the sleeve 15 may be shaped accordingly.

Overall, an illustrative embodiment of the bone fixation device according to the invention may comprise a cranial and a caudal bone plate which are each fixedly connectable to corresponding vertebral bodies by means of two bone screws, and a longitudinal carrier which connects the two bone plates in such a way that they are rotatable in a plane extending approximately parallel to the surface of the bone. The posterior bone screw of each plate may be locked at different angles relative to the axis of the bore by means of a spherical screw head which may be resiliently spread apart by means of a conical straining screw. Thus, instead of having a resiliently spreadable, spherical screw head, the posterior bone screw of each plate may also be fastened by means of a spherical collet chuck arranged in such a way between the bone screw and the bone plate that the bone screw is lockable at different angles relative to the axis of the bore.

For these reasons, the anterior bone screw of each plate is usually screwed in after the respective plates have been inserted and fastened by means of the posterior bone screws. The angle between the bone plate and the corresponding anterior bone screw may be predefined by the bore arranged in the bone plate. However, the connection between the longitudinal carrier and the caudal bone plate usually can be telescopic, thus enabling an angularly stable translation of the cranial bone plate relative to the caudal bone plate. The longitudinal carrier is usually releasably lockable in the caudal bone plate by means of one or several set screws. By contrast, the connection between the cranial bone plate and the longitudinal carrier may be realized by means of a rotation joint with an axis of rotation extending substantially vertically to the bone surface. This rotation joint is also releasably lockable.

The rotation joint may therefore serve for adjusting the angle between the two bone plates. The adjustability of the angle preferably ranges between +30 degrees and −10 degrees. Preferably, the translation and the rotation of the bone plates relative to each other are lockable independently from each other. In addition, the cranial bone plate may be provided with a hexagon socket permitting a torsional moment to be exerted on the bone fixation device. In a first configuration, when the rotation joint is in an unlocked condition, the torsional moment makes it possible to correct the angular position of the cranial vertebra relative to the caudal vertebra. In a second configuration, when the rotation joint is in a locked condition and the anterior bone screw of the caudal plate has not yet been screwed in, the torsional moment may be used to displace the cranial vertebra relative to the caudal vertebra in an anterior direction (retrolisthesis) or a posterior direction (anterolisthesis).

The length of the longitudinal carrier generally may be such that the bone fixation device according to the invention permit fixation of two adjoining vertebral bodies. However, the length of the longitudinal carrier may also be chosen in such a way as to connect two vertebral bodies which are separated from each other by one or several injured vertebral bodies.

The bone fixation device according to the invention may be placed anteroom-laterally and may be used as a mono-segmental or multi-segmental appliance. If necessary, the fixation device may be combined with posterior fixation systems (e.g., bone screws, internal fixator, etc.), so that it is possible to realize even a 360 degrees fixation should the need arise. Moreover, the bone fixation device according to the invention and the tools necessary for assembly of the device are adequately designed so that the device may be implanted either endoscopically or by means of an open operative approach. The principle indications for the use of the bone fixation device according to the invention are trauma, tumors, infections, posttraumatic kyphoses, and vertebral degenerations.

As one of skill in the art might appreciate, the present invention also relates to a method for fixating vertebral bodies. For instance, the implantation of the bone fixation device according to the invention may be realized in observance of the following operative procedures:

The bone screws to be placed posteriorly are screwed into the vertebral bodies that are to be interconnected. In doing so, attention must be paid so that the bone screws are placed as far posteriorly as possible at approximately the same distance from the rear wall of the corresponding vertebra and that they extend more or less parallel to the rear wall of the corresponding vertebra. The caudal bone screw is placed close to the caudal cover plate of the vertebra situated caudally to the injured vertebra. Analogously, the cranial bone screw is positioned close to the cranial cover plate of the vertebra situated cranially to the injured vertebra.

The vertebral bodies are spread apart by means of a spreader placed onto the bone screws. Thus, the vertebral bodies may be maintained at the correct distance from each other and the anatomy of rear wall in the region of the injured vertebra may be reconstructed. An adequately shaped bone onlay is inserted.

The distance between the bone screws is measured, an adequate fixation device is selected, and the selected fixation device is placed onto the inserted bone screws (with the rotation joint and the telescope remaining in a released condition). In case of a scoliotic deformation occurring in the area of the injured vertebra(e), the deformation may be corrected by means of the bone screws. Subsequently, the bone screws are stabilized relative to their angular mobility through locking of the spherical collet chucks.

The individual bone plates are aligned in such a way that each of them extends parallel to the rear wall of the corresponding vertebra. The bone screws to be placed anteriorly are screwed in. In special cases in which the cranial vertebra has slipped anteriorly or posteriorly, only the anterior bone screw of the cranial bone plate may be screwed in. The caudal bone plate may still be connected to the caudal vertebra merely by the bone screw placed posteriorly. For example, prior to the correction of an anterior or posterior displacement of the cranial vertebra relative to the caudal vertebra, the rotation joint must be locked. Subsequently, a torsional moment may be exerted on the hexagon socket formed in the cranial bone plate by means of a corresponding screw driver in order to displace the cranial vertebra anteriorly or posteriorly. In the course of said corrective displacement the entire fixation device turns about the posterior bone screw of the caudal bone plate. After completion of the corrective displacement of the vertebra, the anterior bone screw may be screwed in. Once the second bone screw has been screwed into the caudal bone plate, the vertebra is firmly kept in place in the corrected position and the rotation joint may be released again in order to enable manipulation of the angular position of the cranial vertebra relative to the caudal vertebra.

The anatomically correct angular position of the cranial vertebra relative to the caudal vertebra is reconstructed by means of the hexagon socket arranged in the cranial bone plate and locking of the rotation joint. During the disimpaction of the cranial vertebra the telescopic connector must be freely movable.

The bone onlay is compressed and the telescopic connector is locked.

Additionally, the present invention may have the following features:

One embodiment of the present invention may be a device for connecting a body KA with a body KB. In particular, two bones or bone parts may be so connected. The device may include two plates PA and PB, each of which may have a bottom surface adjoining the bodies KA and KB which are to be connected. Additionally, the plates may have a top surface, and at least one bore penetrating each plate. The bores may penetrate each plate at an angle of between 60 and 90 degrees relative to the bottom surface and may be suitable for receiving an anchoring member by means of which each of the plates may be fastenable to bodies KA and KB, respectively. This device may further include a longitudinal carrier by means of which the two plates are connectable. The connection may be made in such a way that the bottom surfaces of the plates may lie in a common surface and that the distance between the two plates can be adjustable parallel to the common surface. Such a device might possibly be characterized in that the longitudinal carrier can be connected to one of the plates by means of a releasably lockable joint.

For instance, the longitudinal carrier may be connected on one side with one of the plates by means of a releasably lockable joint. The connection between the longitudinal carrier and one of the plates may also allow the longitudinal carrier and the respective plate to be displaced relative to each other. This connection may be releasably lockable. The longitudinal carrier may also be connected with each of the plates by means of a releasably lockable joint. The longitudinal carrier may itself be telescopable, and may be releasably lockable at any required length. The joint may be a hinge joint with an axis of rotation extending essentially perpendicular to the bottom surface. The joint may further comprise a shaft anchored in the longitudinal carrier which is rotatably mounted in a bore arranged concentrically to the axis of rotation in the plate PA or PB, respectively. The shaft may be anchored in the longitudinal carrier through non-positive engagement. Additionally, the shaft may be anchored in the longitudinal carrier through positive engagement.

Additionally, the joint may comprise a shaft anchored concentrically to the axis of rotation in the plate PA or PB, respectively, which shaft may be rotatably mounted in a bore arranged concentrically to the axis of rotation in the longitudinal carrier. In one example, the shaft may be anchored in the plate PA or PB, respectively, through non-positive engagement.

In another example, the shaft may be anchored in the plate PA or PB, respectively, through positive engagement. In another example, the joint may comprise a shaft arranged concentrically to the axis of rotation which is rotatably mounted in the plate PA or PB, respectively, and in the longitudinal carrier.

Furthermore, the shaft may be realized in the form of a sleeve, the sleeve being capable of being resiliently spread apart over a certain segment of its length. A clamping member and a straining means may also be integrated in the sleeve, the clamping member being displaceable relative to the sleeve in a direction parallel to the axis of rotation by means of the straining means, so that as a result of the relative displacement of the clamping member the sleeve is spread apart. The clamping member may form a positive engagement between the longitudinal carrier and the sleeve relative to rotation while being freely movable relative to displacement along the axis of rotation. The clamping member may form a positive engagement between the plate PA or PB, respectively, and the sleeve relative to rotation while being freely movable relative to displacement along the axis of rotation. Two clamping members and a straining means may be integrated in the sleeve, the clamping members being displaceable relative to each other in a direction parallel to the axis of rotation by the action of the straining means, and the sleeve being capable of being spread apart as a result of the displacement of the clamping members. The clamping members may forms a positive engagement between the longitudinal carrier and the sleeve relative to rotation while being freely movable relative to displacement along the axis of rotation. The clamping members may form a positive engagement between the plate PA or PB, respectively, and the sleeve relative to rotation while being freely movable relative to displacement along the axis of rotation.

Moreover, in its spreadable segment the sleeve may be slotted along the axis of rotation. The clamping member(s) may be at least partially wedge-shaped. The sleeve may be at least in part provided with a wedge-shaped slot. The wedge-like forms of the slot and of the clamping member may further be complementary. The half wedge angle may be between 3 and 20 degrees. The half wedge angle may be between 5 and 10 degrees. The straining means may be a threaded bolt, which may be provided with a screw thread. The clamping member may have an internal screw thread complementary to the screw thread of the threaded bolt and that the threaded bolt is mounted within the sleeve in such a way that it is rotatable but axially fixed. The sleeve may have an internal screw thread complementary to the screw thread and that the threaded bolt may be mounted in such a way in the clamping member that it may be rotatable but not axially displaceable relative to the clamping member.

One embodiment of the present invention may be characterized in that one of the clamping members may have an internal screw thread complementary to the screw thread of the threaded bolt and that the threaded bolt may be mounted in the second clamping member in such a way that the threaded bolt may be rotatable but not axially displaceable relative to the clamping member and that the two clamping members may be displaced relative to each other along the axis of rotation as the threaded bolt is rotated.

One embodiment of the present invention may be characterized in that a displacement of the clamping member causes the sleeve to be expanded in its spreadable segment to such an extent that a non-positive engagement is formed between the sleeve and the surrounding wall of the bore.

One embodiment of the present invention may be characterized in that a displacement of the clamping member causes the sleeve to be expanded in its spreadable segment to such an extent that a positive engagement is formed between the sleeve and the surrounding wall of the bore.

One embodiment of the present invention may be characterized in that the positive engagement consists of complementary toothings formed in the resiliently spreadable segment of the sleeve and, correspondingly, on the wall of the bore surrounding the sleeve.

One embodiment of the present invention may be characterized in that the toothings have a pitch angle of between 2 and 6 degrees.

One embodiment of the present invention may be characterized in that the toothings have a pitch angle of between 2.5 and 3.5 degrees.

One embodiment of the present invention may be characterized in that the tips of the teeth of the toothings have an angle of between 60 and 140 degrees.

One embodiment of the present invention may be characterized in that the tips of the teeth of the toothings have an angle of between 90 and 120 degrees.

One embodiment of the present invention may be characterized in that the adjustment of the distance between the plates PA and PB is realized by means of a telescopic appliance.

Another embodiment of the present invention may be characterized in that the plate PA or PB, connected to the longitudinal carrier by means of the rotation joint is provided with a recess which makes it possible, using a tool, to exert a torsional moment on the device about an axis extending essentially vertically to the bottom surface.

Another embodiment of the present invention may be characterized in that the longitudinal carrier has a recess by means of which, using a tool, a torsional moment about an axis extending essentially vertically to the surface formed by the bottom surfaces of the plates PA;PB may be exerted on the device.

Another embodiment of the present invention may be characterized in that the plate PA and the plate PB have each a recess by means of which, using a tool, a torsional moment about an axis extending essentially vertically to the surface formed by the bottom surfaces of the plates PA;PB may be exerted on the device.

Another embodiment of the present invention may be characterized in that it further comprises at least two bone screws and that each of the plates PA;PB is connected to the corresponding body KA;KB by means of at least one bone screw.

Another embodiment of the present invention may be characterized in that it further comprises at least two bone screws and that for each of the plates PA;PB at least one bone screw is releasably lockable at any given angle of up to ±20 degrees relative to a perpendicular to the bottom surface.

Another embodiment of the present invention may be characterized in that for each of the plates PA;PB at least one bone screw is releasably lockable at any given angle ranging between ±15 and ±18 degrees relative to a perpendicular to the bottom surface.

Another embodiment of the present invention may be characterized in that the through hole for the angularly adjustable bone screw formed in the plates PA;PB includes a calotte-shaped segment.

Another embodiment of the present invention may be characterized in that the calotte-shaped segment of the through hole has a roughened surface.

Another embodiment of the present invention may be characterized in that the calotte-shaped segment of the through hole has a structured surface.

Another embodiment of the present invention may be characterized in that the calotte-shaped segment of the through hole has a toothed surface.

Another embodiment of the present invention may be characterized in that the bone screw has a slotted, radially resiliently deformable screw head shaped in the form of a spherical segment.

Another embodiment of the present invention may be characterized in that the spherical segment-like screw head of the bone screw has an accommodation for receiving a straining member for spreading apart the spherical segment-like, slotted screw head.

Another embodiment of the present invention may be characterized in that the receiving accommodation consists of an inner cone divergent towards the opening of the bore and, further down and adjacent thereto, of an internal screw thread, and that the straining member is a screw having an external thread complementary to said internal screw thread and a male taper complementary to said inner cone.

Another embodiment of the present invention may be characterized in that the receiving accommodation consists of a conical, internal screw thread divergent towards the opening of the bore and that the straining member is a screw having an external screw thread complementary to said internal screw thread.

Another embodiment of the present invention may be characterized in that a slotted collet chuck shaped in the form of a spherical segment is integrated in the calotte-shaped segment.

Another embodiment of the present invention may be characterized in that the spherical segment-like collet chuck consists of a softer material than that of the plates PA;PB.

Another embodiment of the present invention may be characterized in that the collet chuck has a structured surface.

Yet another embodiment of the present invention may be characterized in that the collet chuck has a toothed surface.

Yet another embodiment of the present invention may be characterized in that the collet chuck has a roughened surface.

Yet another embodiment of the present invention may be characterized in that the collet chuck has a through hole extending in the direction of the longitudinal axis of the bone screw and having an inner cone divergent towards the bottom surface, the half cone angle being between 3 and 10 degrees.

Yet another embodiment of the present invention may be characterized in that the half cone angle is between 3 and 5 degrees.

Yet another embodiment of the present invention may be characterized in that in the area of the collet chuck the bone screw has an essentially complementary male taper.

Yet another embodiment of the present invention may be characterized in that in the end portion of said male taper, the bone screw has an accommodation for receiving a straining means for chucking the male taper in the inner cone of the collet chuck.

Yet another embodiment of the present invention may be characterized in that the receiving accommodation consists essentially of an internal screw thread while the straining means consists of a screw having an external screw thread complementary to said internal screw thread and a head diameter greater than the smallest diameter of the inner cone of the collet chuck.

Yet another embodiment of the present invention may be characterized in that the receiving accommodation consists essentially of an external screw thread while the straining means consists of a nut having an internal screw thread complementary to said external screw thread and an outside diameter greater than the smallest diameter of the inner cone of the collet chuck.

Yet another embodiment of the present invention may be characterized in that the collet chuck has an internal screw thread and the bone screw a complementary external screw thread.

Yet another embodiment of the present invention may be characterized in that for each of the plates PA;PB at least one bone screw is releasably lockable at a predefined angle of between 70 and 90 degrees relative to the bottom surface of the plates PA;PB.

Yet another embodiment of the present invention may be characterized in that for each of the plates PA;PB at least one bone screw is releasably lockable at a predefined angle of between 80 and 90 degrees relative to the bottom surface of the plates PA;PB.

Yet another embodiment of the present invention may be characterized in that the bone screw insertable at a predefined angle relative to the plate PA;PB has an external screw thread formed in its area of contact with the plate PA;PB which is tightened against the complementary, internal thread formed in the bore of the plate PA;PB.

Yet another embodiment of the present invention may be characterized in that for each of the plates PA;PB at least one bone screw is insertable at any required angle of between 60 and 90 degrees relative to the bottom surface.

Yet another embodiment of the present invention may be characterized in that for each of the plates PA;PB at least one bone screw is insertable at any required angle of between 70 and 90 degrees relative to the bottom surface.

Yet another embodiment of the present invention may be characterized in that the clamping member(s) is (are) at least partially conical.

Yet another embodiment of the present invention may be characterized in that the sleeve is at least in part provided with an inner cone.

Yet another embodiment of the present invention may be characterized in that the conical forms present in the sleeve and on the clamping member are complementary.

Yet another embodiment of the present invention may be characterized in that the half cone angle a is between 3 and 20 degrees.

Yet another embodiment of the present invention may be characterized in that the half cone angle a is between 5 and 10 degrees.

In general, the advantages achieved by the present invention may be considered to consist in the fact that the device usually allows: manipulation of the vertebrae by means of the bone screws in order to correct iatrogenic or other malpositions of the vertebrae; a continuous length adjustment extending over a long distance, thus enabling distraction or compression of the vertebrae within a wide range; and lordosis and kyphosis formation in vivo even after the implant has been inserted.

While various descriptions of the present invention are described above, it should be understood that the various features can be used singly or in any combination thereof. Therefore, this invention is not to be limited to only the specifically preferred embodiments depicted herein. For instance, the longitudinal carrier 7 may comprise rods that are configured to taper or curve over a part of their length for greater stability when the device may be used as a multi-segmental appliance. Similarly, other suitable positive engagement systems may be employed for locking and torsionally driving the rotation joint. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A fixation device for connecting bone portions comprising:
   a first plate and a second plate, each plate having a top surface, a bottom surface for contacting bone, and at least one fixation bore extending from the top surface to the bottom surface;
   at least one member associated with at least one of the plates; and
   a releasably lockable joint,
   wherein the at least one member permits translation of the plates with respect to each other along a translation axis, and the releasably lockable joint permits swivelling of the plates with respect to each other about a swivel axis oriented transverse to the translation axis, and the releasably lockable joint comprises a first clamping member disposed in a sleeve, the first clamping member being configured and dimensioned to exert a force against the sleeve, and at least a portion of the sleeve is resiliently deformable.

2. The fixation device of claim 1, wherein the releasably lockable joint further comprises a straining member for translating the first clamping member with respect to the sleeve.

3. The fixation device of claim 1, wherein each fixation bore is disposed at an angle of about 60° to about 90° with respect to the bottom surface.

4. The fixation device of claim 1, wherein at least a portion of the sleeve and at least a portion of one of the plates are configured and dimensioned for positive engagement with respect to each other.

5. The fixation device of claim 4, wherein the sleeve is disposed in an opening, and the sleeve and opening each have a plurality of teeth for providing positive engagement.

6. The fixation device of claim 1, wherein the at least one member is releasably lockable with at least one of the plates.

7. The fixation device of claim 1, wherein the releasably lockable joint further comprises a second clamping member disposed in the sleeve, the second clamping member being configured and dimensioned to exert a force against the sleeve.

8. The fixation device of claim 7, wherein a straining member is associated with the second clamping member to permit translation of the second clamping member with respect to the sleeve.

9. The fixation device of claim 7, wherein at least one of the clamping members comprises a wedge shape.

10. The fixation device of claim 8, wherein the straining member is threadably associated with the first and second clamping members to permit the members to axially translate with respect to each other.

11. The fixation device of claim 1, wherein the first clamping member comprises a wedge shape and the sleeve comprises a slot configured and dimensioned to positively receive the first clamping member.

12. The fixation device of claim 1, wherein the first clamping member mates with a slot disposed in the sleeve.

13. The fixation device of claim 1, wherein the releasably lockable joint further comprises a straining member for translating the first clamping member with respect to the sleeve, and wherein the straining member comprises a fastener.

14. The fixation device of claim 13, wherein the first clamping member comprises an opening and the fastener is threadably associated with the opening.

15. The fixation device of claim 14, wherein the fastener is axially fixed with respect to the sleeve.

16. The fixation device of claim 1, wherein the sleeve and the first clamping member have complementary conical portions.

17. The fixation device of claim 1, wherein at least one component selected from the first plate, the second plate, and the at least one member includes a recess for positive engagement with a tool to thereby permit rotation of the component about the swivel axis.

18. The fixation device of claim 1, further comprising at least two fixation members, wherein at least one fixation bore in each plate receives a fixation member for coupling the plate to bone.

19. The fixation device of claim 18, wherein at least one of the fixation members may be selectably angulated with respect to the bottom surface of one of the plates.

20. The fixation device of claim 1, wherein at least one fixation bore comprises a spherical portion.

21. The fixation device of claim 20, further comprising at least one fixation member comprising a head with a spherical portion, wherein the spherical portion of the head is sized to rest in the spherical portion of the fixation bore to permit angulation of the fixation member in the fixation bore.

22. The fixation device of claim 21, wherein the spherical portions are mutually roughened, structured, or toothed.

23. The fixation device of claim 21, wherein the head is slotted and resiliently deformable.

24. The fixation device of claim 23, further comprising a straining member for circumferentially deforming the head.

25. The fixation device of claim 24, wherein the head further comprises a threaded inner cone threadably associated with the straining member.

26. The fixation device of claim 20, further comprising a collet chuck having an outer spherical portion, wherein the spherical portions of the at least one fixation bore and collet chuck mate to permit angulation of the portions with respect to each other.

27. The fixation device of claim 26, wherein the collet chuck further comprises a through hole for receiving a fixation member.

28. The fixation device of claim 27, wherein the through hole comprises a first taper, the fixation member comprises a second taper, and the tapers are complementary.

29. The fixation device of claim 1, wherein the swivel axis is oriented substantially perpendicular to the bottom surface of at least one of the plates.

30. The fixation device of claim 1, wherein the releasably lockable joint comprises a shaft coupled to one of the plates and one of the at least one member, the shaft permitting rotation of the plate with respect to the member.

31. The fixation device of claim 30, wherein at least a portion of the shaft is configured and dimensioned for positive engagement with at least one of the plate and the member.

32. The fixation device of claim 1, wherein the at least one member is fixably connected with at least one of the plates.

33. The fixation device of claim 32, wherein the at least one member is integrally connected with at least one of the plates.

34. The fixation device of claim 1, wherein the at least one member is telescopically associated with at least one of the plates.

35. A fixation device for connecting bone portions comprising
- a first plate and a second plate each plate having a top surface, a bottom surface for contacting bone, and at least one fixation bore extending from the top surface to the bottom surface, at least one of the plates having a channel;
- at least one longitudinal member slidably associated with the channel in at least one of the plates; and
- a releasably lockable joint located in a joint bore below the top surface of at least one of the bone plates,
- wherein the at least one longitudinal member permits translation of the plates with respect to each other along a translation axis, and the releasably lockable joint permits swivelling of the plates with respect to each other about a swivel axis oriented transverse to the translation axis.

36. The fixation device of claim 35, wherein at least one component selected from the first plate, the second plate, and the at least one longitudinal member includes a recess for positive engagement with a tool to thereby permit rotation of the component about the swivel axis.

37. The fixation device of claim 36, further comprising at least two fixation members, wherein at least one fixation bore in each plate receives one of the fixation members fir coupling the plate to bone.

38. A fixation device for connecting bone portions comprising:
- first and second plates, each plate having a top surface, a bottom surface for contacting bone, and a fixation bore extending from the top surface to the bottom surface;
- first and second members, each member being slidably associated with the first plate and second plate respectively; and a releasibly joint defining a first axis and comprising a clamping member disposed in a sleeve, wherein the members permit translation of the plates with respect to each other, the joint permits angulation of one of the plates with respect to at least one of the members about the first axis, and clamping is ac able with respect to the sleeve to releasably fix the angulation, the sleeve is located in a joint bore, and the joint is located above the bottom surface of at least one of the plates.

39. The fixation device of claim 38, wherein the clamping member comprises a wedge shape and the sleeve comprises a slot configured and dimensioned to positively receive the clamping member.

40. The fixation device of claim 39, wherein the clamping member mates with the slot.

41. The fixation device of claim 38 wherein the releasably lockable joint further comprises a straining member for translating the clamping member with respect to the sleeve, and wherein the straining member comprises a fastener.

42. The fixation device of claim 41, wherein the clamping member comprises an opening and the fastener is threadably associated with the opening.

43. The fixation device of claim 38, wherein at least one component selected from the first plate, the second plate, and the first and second members includes a recess for positive engagement with a tool to thereby permit rotation of the component about the first axis.

44. The fixation device of claim 43, further comprising at least two fixation members, wherein at least one fixation bore in each plate receives a fixation member for coupling the plate to bone.

45. A method for internal fixation of first and second vertebral bodies comprising the steps of:

securing a bone fastening element posteriorly into each vertebral body;

displacing one vertebral body with respect to the other;

passing the fastening element secured into the first vertebral body through a first fixation bore on the first plate of the fixation device of claim 1;

passing the fastening element secured into the second vertebral body through a first fixation bore on the second plate of the fixation device of claim 1;

passing another fastening element through a second fixation bore in the first plate into the first vertebral body;

passing another fastening element through a second fixation bore in the second plate into the second vertebral body;

manipulating the first vertebral body relative to the second vertebral body; and locking the releasably lockable joint of the fixation device of claim 1.

46. The method of claim 45, wherein manipulating the vertebral bodies includes both translation and rotation of the first vertebral body with respect to the second vertebral body.

47. The method of claim 45, wherein manipulating the vertebral bodies restores an anatomically correct angular position of the first vertebral body relative to the second vertebral body.

* * * * *